(12) United States Patent
Avalle

(10) Patent No.: US 6,893,646 B2
(45) Date of Patent: May 17, 2005

US006893646B2

(54) COATED COSMETIC POWDER

(75) Inventor: Nadia Avalle, Milan (IT)

(73) Assignee: Intercos Italia S.p.A. (IT)

( * ) Notice: Subject to any disclaimer, the term of this patent is extended or adjusted under 35 U.S.C. 154(b) by 0 days.

(21) Appl. No.: 09/800,463

(22) Filed: Mar. 8, 2001

(65) Prior Publication Data
US 2001/0031271 A1 Oct. 18, 2001

(30) Foreign Application Priority Data
Mar. 9, 2000 (IT) .................................... MI2000A0465

(51) Int. Cl.⁷ ............................ A61K 7/00; A61K 9/28; A61K 9/16; B05D 7/00; B32B 9/04
(52) U.S. Cl. ....................... 424/401; 424/473; 424/489; 424/490; 427/214; 428/402.24; 428/403; 428/407
(58) Field of Search ................................ 424/489, 490, 424/474, 401; 427/214; 428/402.24, 403, 407

(56) References Cited

U.S. PATENT DOCUMENTS

| 3,969,547 | A | * | 7/1976 | Isawa et al. ................. 427/214 |
| 5,153,174 | A | * | 10/1992 | Band et al. .................... 514/12 |
| 5,879,688 | A | * | 3/1999 | Coury et al. ................. 424/401 |
| 5,958,458 | A | * | 9/1999 | Norling et al. ............. 424/490 |
| 6,120,787 | A | * | 9/2000 | Gustafsson et al. ......... 424/426 |
| 6,183,783 | B1 | * | 2/2001 | Benoit et al. ................ 424/497 |
| 6,187,439 | B1 | * | 2/2001 | Elwakil ....................... 428/407 |

FOREIGN PATENT DOCUMENTS

| EP | 0 447 318 A | 9/1991 |
| EP | 0 882 443 A | 12/1998 |
| FR | 2 657 255 A | 7/1991 |
| JP | XP-002263516 | 2/1991 |

* cited by examiner

Primary Examiner—Shengjun Wang
(74) Attorney, Agent, or Firm—Akerman Senterfih

(57) ABSTRACT

The present invention refers to a cosmetic powder whose coating includes polymers or co-polymer belonging to the Poly Alpha Hydroxi Acids family, to a cosmetic composition that contains it and to the process of preparation of the powder.

11 Claims, No Drawings

COATED COSMETIC POWDER

This application claims foreign priority of ITALY MI2000A000465, filed Mar. 9, 2000.

DESCRIPTION

The present invention refers to a coated cosmetic powder, in particular with Poly Hydroxi Alpha Acids, to a cosmetic composition that contains it and to the process for the preparation of the powder.

Cosmetic powders, both of organic as well as inorganic nature are a fundamental part in the preparation of make-up cosmetics, for instance make-up powders, eye shadows, foundation creams, lipsticks, etc. By applying these products on the skin a coloured film is formed that is aimed at hiding inaestheticisms, and at giving a visibly more attractive aspect.

This film is deposited on the surface of the skin, therefore the powders are directly in contact with the surface layers of the same. Such contact can interfere with the normal physiological activity of the skin, with possible consequences as unpleasant feeling on behalf of the user, and sometimes with irritating and occluding effects.

The skin is an essential organ of the human body, that is subject to external and internal influences by acting as a protecting organ (mechanical, thermal, physical, chemical protection) and is provided with extreme sensitivity.

It is therefore very important to know and to interpret deeply its needs, not only for decorative purposes but, above all according to modern make-up trends, it is necessary to protect it and to help it maintain itself young.

From approximately fifty years it has been known that one of the elements essential to these purposes is its natural content in humidity (N.M.F. Natural Moisture Factor), composed as follows:

Amino-acids 40.0%

PCA 12.0%

Lactate 12.0%

Urea 7.0%

NH2, uric acid, glucosamine, creatinine 1.5%

Citrate 0.5%

Na, K, Ca, Mg, $PO_4$, US 18.5%

Sugars, organic acids, peptides, unidentified material 8.5%

This natural N.M.F, of such great importance for the quality of the skin, can be increased through external means.

By analysing its composition the presence of citrate and above all of Lactate (12%), that are respectively the salt forms of citric and lactic acid is evident.

Consequently our concern was to study the Alpha Hydroxi Acids (lactic, glycolic, salicylic, acetic, citric acid etc), as active agents that allow, on the medium-long term, the cellular renewal and a surface exfoliation, that eliminates dead cells and impurities, thus making the skin clear and smooth, ready to assume curative elements and to evidence make-up.

In order to take advantage of their undeniable effectiveness at best, our researches have been directed to the study of the use of such acids in make-up, and in particular in anhydrous products. The incorporation of such acids in anhydrous products is difficult if not impossible since they are water-soluble and in addition they are potentially irritating.

In view of the state of the art herein described, scope of the present invention is to realise a cosmetic product that contains elements belonging to the poly alpha hydroxi acids family.

According to the present invention, such scope is attained with the realisation of a cosmetic powder with which a coating is associated, characterised in that said coating includes polymers or co-polymers belonging to the poly alpha hydroxi acids family.

Such scope is also attained by means of a cosmetic composition that comprises at least one cosmetic powder with which a coating is associated, characterised in that said coating is made up of polymers or co-polymers belonging to the poly Alpha hydroxi acids family.

In addition such scope is attained by means of a process for the preparation of a cosmetic powder comprising the following stages:

preparation of a polymer or co-polymer phase of alpha hydroxi acids, mixture of said powder phase and of said polymer or co-polymer phase of alpha hydroxi acids with a solvent in slurry or in spray, evaporation of the solvent.

Owing to the present invention it is possible to realise a powder coated with polymers or co-polymer belonging to the family of the alpha hydroxi acids, that, being inserted in a cosmetic product in particular make-up, once it is applied, the direct contact between the poly alpha hydroxi acids and the epidermis is facilitated. Such polymers or co-polymers, since they are biodegradable, once they come to contact with the skin, and as a consequence with the humidity (water) contained in it added the humidity absorbed from the environment, slowly degrade thus freeing olygomeric, monomeric fractions and other possible hydrophilic/lipophilic active principles, previously incorporated in the coating phase. The coating of the powders with polymers or co-polymers of the alpha hydroxi acids, modifies its surface chemical-physical characteristics, making them more compatible with the skin. In addition, such coating allows the incorporation of the alpha hydroxi acids in a cosmetic product, that if differently incorporated would be particularly weak and unstable.

For instance, by using the poly DL-Lactide, as a powder coating, its hydrolysis leads to the formation of lactic acid, that besides, as mentioned above, is one of the main components of the N.M.F.

The advantages of the present invention will become evident from the following description of several embodiments thereof, non-limiting, that are illustrated as an example.

A powder according to the present invention to which a coating is associated includes:

a) a powder phase comprised in weight between 0.1÷99.90%, preferably between 60÷99%, b) a polymer/co-polymer phase of alpha hydroxi acids comprised in weight within 0.0001÷60%, preferably between 0.1÷20%.

Possibly the alpha hydroxi acids polymer/co-polymer phase can also incorporate lipid/hydrophilic functional substances and/or vitamins/aminoacids, in this case the amount in weight of this phase, also called coating phase, is comprised between 0.001÷80% and preferably between 1÷30%.

The powder phase a) can be made up of excipients and pigments used singularly or in mixtures. As excipients it is possible to use for instance Talc, Mica, Kaolin, Nylon, spherical and non-spherical silica, starches and its derivatives. As pigments it is possible to use for instance Titanium Dioxide, Zinc Oxides, Iron Oxides, Lakes, Ultramarine blue and pink, Carmine, Manganese Violets, and in any case lacquers and pigments of others organic and inorganic dies reported in the CTFA and the CLS. In addition the powder phase can also contain silicones and its derivatives as Oils, Waxes, Surfactants, Perfluorates.

To the polymer/co-polymer phase of alpha Hydroxi acids b) other functional substances for example Octyldodecyl Lactate, Isononyl Isononanoate, Octyldodecyl Stearoyl Stearate are preferably aggregable.

In addition to the polymers/co-polymers of alpha hydroxi acids some active principles are also aggregable, for instance vitamins and/or amino acids.

The process for the preparation of a coated powder to be utilised in a cosmetic composition, according to the present invention, is carried out by means of a mixture of the polymers/co-polymers of alpha hydroxi acids with the powder owing to the use of solvents such as Ethyl Acetate, Ethyl Lactate, Methylene Chloride, Esters with low molecular weight. Such mixing is preferably carried out using the Slurry technique (that is formation of a powder/solvent mixture that is kept in agitation) or the Spray technique (that is to <<atomise>> the solution containing the properly dissolved coating, onto the powder phase that is kept in motion) and subsequent evaporation of the solvent.

A cosmetic composition, according to the present invention, comprises at least a powder coated with polymers or co-polymer belonging to the poly alpha hydroxi acids family, in combination with other typical ingredients of the composition.

Hereinafter there are reported some non-limiting examples of coated powders and cosmetic compositions according to the present invention.

EXAMPLE NO. 1

TABLE 1

| Powder phase | 970 g | Talc | 88% in weight |
|---|---|---|---|
| | | Nylon | 5.5% in weight |
| | | spherical Silica | 6.5% in weight |
| Coating Phase | 30 g | Poly (DL-Lactide) | |

To the powder phase composed as in table 1, with a weight of 970 g., 970 g. of Ethyl Acetate have been added and mixed, by means of mechanical agitator, for 10'.

300 g. of a 10% solution of Poly (DL-Lactide) in Ethyl Acetate, previously prepared at 50° C. under agitation are added to this dispersion. This is left mixing for 10', then it is dried at 80° C.

Subsequently the powder thus coated is sifted preferably at 200 Mesh.

EXAMPLE NO. 2

TABLE 2

| Powder phase | 980 g | Superior Talc | 817.21 g |
|---|---|---|---|
| | | Titanium Dioxide | 18.42 g |
| | | Bismuth Oxychloride | 28.42 g |
| | | Yellow Iron Oxides | 18.95 g |
| | | Brown Iron Oxides | 22.10 g |
| | | Black Iron Oxides | 1.58 g |
| | | Red Iron Oxides | 7.52 g |
| | | Nylon | 18.95 g |
| | | Spherical Silica | 36.85 g |
| Coating phase | 20 g | DL-Lactide/Glycolide | |

To the powder phase composed as in table 2, with a weight of 980 g., 980 g. of Ethyl Acetate have been added and mixed, through mechanical agitator.

200 g. of a 10% solution of Poly DL-Lactide-co-Glycolide in Ethyl Acetate, previously prepared at 50° C. under agitation, are added to this mixture. This is agitated for 10', then it is dried at 80° C.

Subsequently the powder thus coated is sifted preferably at 200 Mesh.

EXAMPLE NO. 3

TABLE 3

| Powder phase | 990 g | Talc |
|---|---|---|
| Coating Phase | 10 g | Poly-L-Lactide |

To the powder phase composed of 990 g. of talc, 990 g. of Ethyl Acetate have been added and mixed, through mechanical agitator, for 10'.

100 g. of a 10% Poly-L-Lactide solution in Ethyl Acetate, previously prepared at 50° C. under agitation, are added to this dispersion. This is agitated for 10', then it is dried at 80° C.

Subsequently the powder thus coated is sifted preferably at 200 Mesh.

EXAMPLE NO. 4

TABLE 4

| Powder phase | 970 g | Talc | 88% in weight |
|---|---|---|---|
| | | Nylon | 5.5% in weight |
| | | spherical Silica | 6.5% in weight |
| Coating Phase | 7.50 g | Poly (DL-Lactide) | |
| | 22.50 g | Isononyl Isononanoate | |

To the phase powder composed as in table 4, with a weight of 970 g., 970 g. of Ethyl Acetate have been added and mixed, through mechanical agitator, for 10'.

92.5 g. of a 10% Poly (DL-Lactide) solution in Ethyl Lactate, previously prepared at 90° C. under agitation, are added to this dispersion. This is agitated for 10', then it is dried at 80° C.

Subsequently the powder thus coated is sifted preferably at 200 Mesh.

EXAMPLE NO. 5

TABLE 5

| Powder phase | 970.00 g | Talc | 88% in weight |
|---|---|---|---|
| | | Titanium Dioxide | 20% in weight |
| | | Nylon | 5.5% in weight |
| | | Spherical Silica | 6.5% in weight |
| Coating Phase | 15.00 g | Poly (DL-Lactide) | |
| | 15.00 g | Octyldodecyl Lactate | |

To the phase powder composed as in table 5, with a weight of 970 g., 970 g. of Acetate of Ethyl have been added and agitated, through mechanical agitator, for 10'.

165 g. of a solution composed of 150 g of a 10% Poly (DL-Lactide) solution in Ethyl Lactate, previously prepared at 90° C. and of 15 g of Octyldodecyl Lactate are added to this dispersion. This is agitated for 10', then it is dried at 80° C.

Subsequently the powder thus coated is sifted preferably at 200 Mesh.

EXAMPLE NO. 6

TABLE 6

| Powder phase | 970.00 g | Talc | 88% in weight |
|---|---|---|---|
| | | Titanium Dioxide | 20% in weight |
| | | Orgasol | 5.5% in weight |
| | | spherical Silica | 6.5% in weight |
| Coating Phase | 7.50 g | Poly (DL-Lactide) | |
| | 17.50 g | Octyldodecyl Lactate | |
| | 5.00 g | Vitamin A | |

To the powder phase composed as in table 6, with a weight of 970 g., 970 g. of Ethyl Acetate they have been added that are mixed, through mechanical agitator, for 10'.

97.5 g. of a solution composed of 75 g of a 10% solution of Poly (DL-Lactide) in Ethyl Acetate, previously prepared at 75° C. and of 17.5 g of Octyldodecyl Lactate are added to this dispersion. This is agitated for 10', then it is dried at 80° C.

Subsequently the powder thus coated is sifted preferably at 200 Mesh.

EXAMPLE NO. 7

A compact powder foundation according to the formula reported in table 7 that contains coated pigments (yellow Iron Oxide, red Iron Oxide, black Iron Oxide coated with Poly (DL-Lactide), has been prepared with the same procedure of the examples 1÷4.

TABLE 7

| Coated Talc | 44.2% |
|---|---|
| Coated Pearls (Titanium/Mica) | 3.0% |
| Coated Titanium Dioxide | 10.0% |
| Coated yellow Iron Oxide | 8.0% |
| Coated red Iron Oxide | 3.6% |
| Coated black Iron Oxide | 2.5% |
| Silica | 2.5% |
| Nylon 12 | 3.0% |
| Bismuth Oxychloride | 1.5% |
| Myristate Magnesium | 2.0% |
| Preservative | 0.5% |
| Dimethicone | 4.0% |
| Isononyl Isononanoate | 9.0% |
| Octyldodecyl Stearoyl Stearate | 3.0% |
| Perfume | 0.2% |

EXAMPLE NO. 8

An eye shadow powder according to a formula reported in table 8 using coated pigments, has been prepared with the same procedure of examples 1÷6.

TABLE 8

| Coated Talc | 61.74% |
|---|---|
| Coated Pearls (Titanium/Mica) | 10.5% |
| Coated Titanium Dioxide | 2.2% |
| Coated yellow Iron Oxide | 1.6% |
| Coated red Iron Oxide | 0.16% |
| Coated black Iron Oxide | 0.8% |
| Silica | 2.5% |
| Nylon 12 | 3.0% |
| Preservative | 0.5% |
| Dimethicone | 4.0% |
| Isostearyl Lactate | 8.0% |
| Octyldodecyl stearoyl stearate | 3.0% |

EXAMPLE NO. 9

A lipstick according to the formula reported in table 9, that contains pigments coated with Poly Hydroxi Alpha Acids, has been prepared with the same procedure of examples 1÷6.

TABLE 9

| Fatty lipstick base | 80.00% |
|---|---|
| Castor Oil | as much as suffices 100 |
| Pentaerythrityl Tetraisostearate | 3.50% |
| Candelilla Wax | 1.20% |
| Coated Red Iron Oxide | 3.00% |
| Coated Titanium Dioxide | 6.26% |
| Coated FD&C Red 7 Al Lake | 0.35% |
| Coated FD&C Blue 1 | 0.42% |
| Coated Pearls (Titanium/Mica) | 5.00% |

EXAMPLE NO. 10

A fluid foundation cream with external oil/silicone phase, according to the formula reported in table 10, that contains pigments coated with Poly Hydroxi Alpha Acids, has been prepared with same procedure 1÷6.

TABLE 10

| Microcrystalline Wax | 2.00% |
|---|---|
| Hydrogenated Castor Oil | 0.60% |
| Silicone Derivatives | 12.9% |
| Cyclomethicone | as much as suffices 100 |
| Coated Talc | 2.50% |
| Coated Pigments | 13.0% |
| Polyglyceryl-4 Isostearate | 1.50% |
| Octil Metossicinnamate | 2.0% |
| Fonossiethanl | 0.80% |
| Silica | 2.00% |
| Isononyl Isononanoate | 5.00% |
| $H_2O$ | 43.00% |
| Propylene Glycol | 4.00% |
| NaCl | 2.00% |
| Glycerine | 1.00% |

What is claimed is:

1. A cosmetic powder comprising:

a powder comprising at least one of the group consisting of talc, mica, kaolin, nylon, pigments, and spherical and non-spherical silica; and a coating applied to the powder, wherein the coating comprises at least one alpha hydroxy acid polymer or copolymer whereby said alpha hydroxy acid polymer or copolymer can degrade and release onto the skin of a wearer at least one of monomers and oligomers on application of said cosmetic powder to the skin, wherein said alpha hydroxy acid polymer or copolymer is in a quantity between 0.1 to 20% by weight of the coated cosmetic powder; and said power is in a quantity between 60 to 99% by weight of the coated cosmetic powder.

2. The cosmetic powder according to claim 1, wherein said coating includes poly DL-lactide.

3. The cosmetic powder according to claim 1, wherein said coating includes at least one of lipid, lipophilic and hydrophilic functional substances.

4. The cosmetic powder according to claim 1, wherein said coating includes at least one of vitamins and amino acids.

5. Cosmetic composition containing at least one cosmetic powder according to claim 1.

6. A process for the preparation of a cosmetic powder comprising the steps of:

preparation of a powder phase, wherein said powder phase comprises at least one of the group consisting of talc, mica, kaolin, nylon, pigments, and spherical and non-spherical silica;

preparation of an alpha hydroxy acids polymer or co-polymer phase;

mixture of said powder phase and of said alpha hydroxy acids polymer or co-polymer phase with a solvent in slurry or spray; and evaporation of the solvent, to form an alpha hydroxy acids polymer or co-polymor coating on said powder, whereby said coating can degrade and release onto the skin of a wearer at least one of monomers and oligomers on application of said cosmetic powder to the skin;

wherein the alpha hydroxy acid polymer or copolymer is in a quantity between 0.1 to 20% by weight of the coated cosmetic powder; and said powder is in a quantity between 60 to 99% by weight of the coated cosmetic powder.

7. The process according to claim 6, wherein said solvent is ethyl acetate.

8. The process according to claim 6, further comprising the step of mixing said alpha hydroxy acids polymer or co-polymer phase with at least one of lipid, lipophilic and hydrophilic functional substances.

9. The process according to claim 6, further comprising the step of mixing said alpha hydroxy acids polymer or co-polymer phase with at least one of vitamins and amino acids.

10. The cosmetic powder according to claim 3, comprising said coating in a quantity between 0.001 and 80% by weight.

11. The cosmetic powder according to claim 10, comprising said coating in a quantity between about 1 and 30% by weight.

* * * * *

UNITED STATES PATENT AND TRADEMARK OFFICE
CERTIFICATE OF CORRECTION

PATENT NO. : 6,893,646 B2
APPLICATION NO. : 09/800463
DATED : May 17, 2005
INVENTOR(S) : Avalle It is certified that error appears in the above-identified patent and that said Letters Patent is hereby corrected as shown below:

Item [73]
In the Assignee, replace "Intercos Italia S.p.A." with --Intercos S.p.A.--

Signed and Sealed this

Thirtieth Day of January, 2007

JON W. DUDAS
*Director of the United States Patent and Trademark Office*